(12) United States Patent
Beckham

(10) Patent No.: US 8,323,242 B2
(45) Date of Patent: Dec. 4, 2012

(54) NON-COMPLIANT MEDICAL BALLOON HAVING A LONGITUDINAL FIBER LAYER

(75) Inventor: James P. Beckham, Athens, TX (US)

(73) Assignee: C.R. Bard, Inc., Tempe, AZ (US)

( * ) Notice: Subject to any disclaimer, the term of this patent is extended or adjusted under 35 U.S.C. 154(b) by 217 days.

(21) Appl. No.: 12/693,931

(22) Filed: Jan. 26, 2010

(65) Prior Publication Data

US 2010/0179581 A1    Jul. 15, 2010

Related U.S. Application Data

(60) Continuation-in-part of application No. 11/551,339, filed on Oct. 20, 2006, and a continuation-in-part of application No. 11/551,326, filed on Oct. 20, 2006, now Pat. No. 7,927,443, each which is a division of application No. 10/726,960, filed on Dec. 3, 2003, now abandoned, which is a continuation of application No. 09/523,817, filed on Mar. 13, 2000, now Pat. No. 6,746,425, which is a continuation-in-part of application No. 08/873,413, filed on Jun. 12, 1997, now abandoned.

(60) Provisional application No. 60/019,931, filed on Jun. 14, 1996.

(51) Int. Cl.
*A61M 31/00* (2006.01)

(52) U.S. Cl. .......... 604/103.09; 604/103.13; 604/103.06

(58) Field of Classification Search .............. 604/95.04, 604/96.01, 103.06–103.13, 508, 509
See application file for complete search history.

(56) References Cited

U.S. PATENT DOCUMENTS

| | | | |
|---|---|---|---|
| 3,023,982 A | 3/1962 | Huch | |
| 4,367,396 A | 1/1983 | Ravinsky | |
| 4,482,516 A | 11/1984 | Bowman et al. | |
| 4,572,186 A | 2/1986 | Gould et al. | |
| 4,637,396 A | 1/1987 | Cook | |
| 4,646,742 A * | 3/1987 | Packard et al. | 606/194 |
| 4,702,252 A | 10/1987 | Brooks et al. | |
| 4,706,670 A | 11/1987 | Andersen et al. | |
| 4,796,629 A | 1/1989 | Grayzel | |
| 4,808,465 A | 2/1989 | Vane | |
| 4,952,357 A | 8/1990 | Euteneuer | |
| 5,066,285 A | 11/1991 | Hillstead | |
| 5,078,727 A | 1/1992 | Hannam et al. | |
| 5,108,415 A | 4/1992 | Pinchuk et al. | |
| 5,108,416 A | 4/1992 | Ryan et al. | |
| 5,112,304 A | 5/1992 | Barlow et al. | |

(Continued)

FOREIGN PATENT DOCUMENTS

WO    WO 95/18647    7/1995

OTHER PUBLICATIONS http://en.wikipedia.org/wiki/Nylon.

(Continued)

*Primary Examiner* — Victoria P Shumate
(74) *Attorney, Agent, or Firm* — King & Schickli, PLLC

(57) ABSTRACT

A non-compliant medical balloon is formed with a first fiber layer including a first fiber and a second fiber layer over said first fiber layer. The first fiber is substantially parallel to a longitudinal axis of the non-compliant medical balloon.

39 Claims, 9 Drawing Sheets

U.S. PATENT DOCUMENTS

| | | |
|---|---|---|
| 5,116,360 A | 5/1992 | Pinchuk et al. |
| 5,171,297 A | 12/1992 | Barlow et al. |
| 5,192,296 A * | 3/1993 | Bhate et al. ................... 606/194 |
| 5,201,706 A | 4/1993 | Noguchi et al. |
| 5,207,700 A | 5/1993 | Euteneuer |
| 5,264,260 A | 11/1993 | Saab |
| 5,270,086 A | 12/1993 | Hamlin |
| 5,290,306 A | 3/1994 | Trotta et al. |
| 5,295,960 A | 3/1994 | Aliahmad et al. |
| 5,304,340 A | 4/1994 | Downey |
| 5,306,246 A | 4/1994 | Sahatjian et al. |
| 5,314,443 A | 5/1994 | Rudnick |
| 5,330,429 A | 7/1994 | Noguchi et al. |
| 5,338,299 A | 8/1994 | Barlow |
| 5,344,401 A | 9/1994 | Radisch et al. |
| 5,358,486 A | 10/1994 | Saab |
| 5,451,209 A | 9/1995 | Ainsworth et al. |
| 5,453,076 A | 9/1995 | Kiyota et al. |
| 5,470,314 A | 11/1995 | Walinsky |
| 5,477,886 A | 12/1995 | Van Beugen et al. |
| 5,478,320 A | 12/1995 | Trotta |
| 5,492,532 A | 2/1996 | Ryan et al. |
| 5,549,552 A | 8/1996 | Peters et al. |
| 5,554,120 A | 9/1996 | Chen et al. |
| 5,556,382 A | 9/1996 | Adams |
| 5,587,125 A | 12/1996 | Roychowdhury |
| 5,599,576 A | 2/1997 | Opolski |
| 5,620,649 A | 4/1997 | Trotta |
| 5,647,848 A | 7/1997 | Jorgensen |
| 5,728,063 A | 3/1998 | Preissman et al. |
| 5,752,934 A | 5/1998 | Campbell et al. |
| 5,755,690 A | 5/1998 | Saab |
| 5,759,172 A | 6/1998 | Weber et al. |
| 5,769,817 A | 6/1998 | Burgmeier |
| 5,772,681 A | 6/1998 | Leoni |
| 5,788,979 A | 8/1998 | Alt et al. |
| 5,797,877 A | 8/1998 | Hamilton et al. |
| 5,820,613 A | 10/1998 | Van Werven-Franssen et al. |
| 5,868,779 A | 2/1999 | Ruiz |
| 5,879,369 A | 3/1999 | Ishida |
| 5,928,181 A | 7/1999 | Coleman et al. |
| 5,972,441 A | 10/1999 | Campbell et al. |
| 6,007,544 A | 12/1999 | Kim |
| 6,010,480 A | 1/2000 | Abele et al. |
| 6,012,457 A | 1/2000 | Lesh |
| 6,024,722 A | 2/2000 | Rau et al. |
| 6,024,740 A | 2/2000 | Lesh et al. |
| 6,027,779 A | 2/2000 | Campbell et al. |
| 6,036,697 A | 3/2000 | DiCaprio |
| 6,117,101 A | 9/2000 | Diederich et al. |
| 6,124,007 A | 9/2000 | Wang et al. |
| 6,127,597 A | 10/2000 | Beyar et al. |
| 6,132,824 A * | 10/2000 | Hamlin ........................ 428/35.2 |
| 6,156,254 A | 12/2000 | Andrews et al. |
| 6,164,283 A | 12/2000 | Lesh |
| 6,171,297 B1 | 1/2001 | Pedersen et al. |
| 6,183,492 B1 | 2/2001 | Hart et al. |
| 6,187,013 B1 | 2/2001 | Stoltze et al. |
| 6,213,995 B1 | 4/2001 | Steen |
| 6,234,995 B1 | 5/2001 | Peacock, III |
| 6,245,064 B1 | 6/2001 | Lesh et al. |
| 6,254,599 B1 | 7/2001 | Lesh et al. |
| 6,263,236 B1 | 7/2001 | Kasinkas et al. |
| 6,270,902 B1 | 8/2001 | Tedeschi et al. |
| 6,290,485 B1 | 9/2001 | Wang |
| 6,305,378 B1 | 10/2001 | Lesh |
| 6,315,751 B1 | 11/2001 | Cosgrove et al. |
| 6,328,925 B1 | 12/2001 | Wang et al. |
| 6,450,989 B2 * | 9/2002 | Dubrul et al. ................. 604/104 |
| 6,626,889 B1 | 9/2003 | Simpson et al. |
| 6,702,782 B2 | 3/2004 | Miller et al. |
| 6,905,743 B1 | 6/2005 | Chen et al. |
| 6,911,038 B2 | 6/2005 | Mertens et al. |
| 6,977,103 B2 | 12/2005 | Chen et al. |
| 7,156,860 B2 * | 1/2007 | Wallsten ........................ 606/192 |
| 7,252,650 B1 * | 8/2007 | Andrews et al. ......... 604/103.06 |
| 7,309,324 B2 | 12/2007 | Hayes |
| 7,354,419 B2 | 4/2008 | Davies |
| 7,635,510 B2 | 12/2009 | Horn |
| 8,002,744 B2 | 8/2011 | Pepper |
| 2001/0016726 A1* | 8/2001 | Dubrul et al. ................. 604/509 |
| 2002/0161388 A1 | 10/2002 | Samuels |
| 2002/0193820 A1* | 12/2002 | Wakuda et al. ............... 606/194 |
| 2003/0149468 A1* | 8/2003 | Wallsten ...................... 623/1.11 |
| 2003/0195490 A1* | 10/2003 | Boatman et al. .............. 604/525 |
| 2004/0176740 A1 | 9/2004 | Chouinard |
| 2005/0102020 A1 | 5/2005 | Grayzel |
| 2005/0271844 A1 | 12/2005 | Mapes |
| 2006/0085022 A1 | 4/2006 | Hayes et al. |
| 2008/0183132 A1 | 7/2008 | Davies |

OTHER PUBLICATIONS http://en.wikipedia.org/wiki/Fibers.
Office Action dated Sep. 1, 2011 in U.S. Appl. No. 12/979,843 to Beckham.
Office Action dated Mar. 9, 2012 in U.S. Appl. No. 12/979,843 to Beckham.
U.S. Appl. No. 12/979,843 Office Action dated Sep. 14, 2012.
U.S. Appl. No. 13/299,988 Office Action dated Sep. 27, 2012.

* cited by examiner

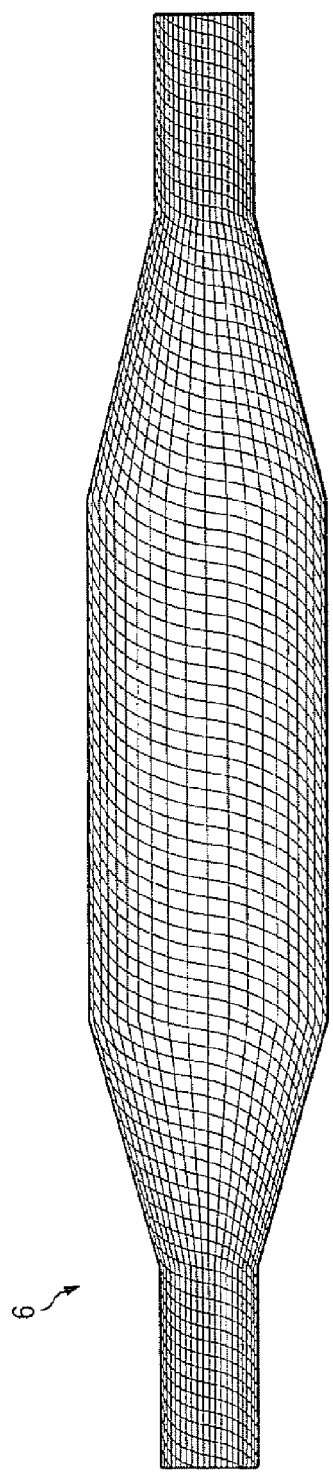
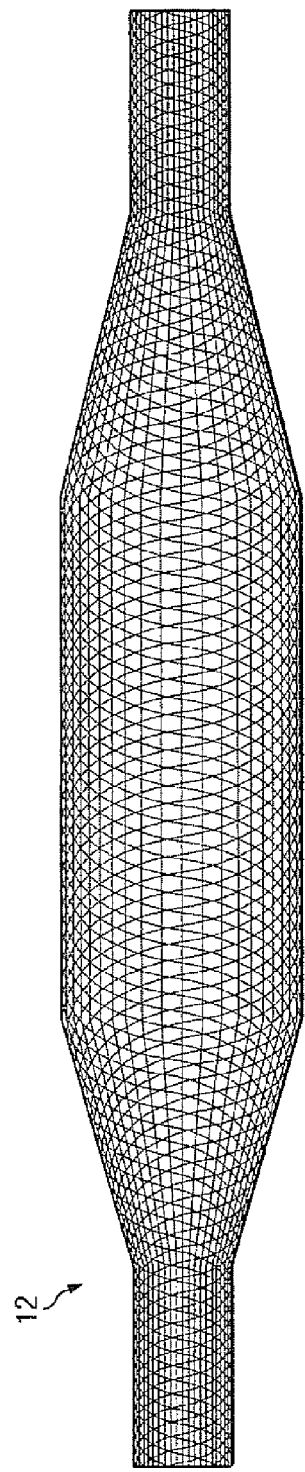
FIG. 3
FIG. 4

NON-COMPLIANT MEDICAL BALLOON HAVING A LONGITUDINAL FIBER LAYER

This application claims priority as a continuation-in-part of U.S. patent application Ser. No. 11/551,339; entitled "Medical Balloon," and also as a continuation-in-part of U.S. patent application Ser. No. 11/551,326, entitled "Medical Balloon," each of which being divisionals of U.S. patent application Ser. No. 10/726,960, which is a continuation of U.S. patent application Ser. No. 09/523,817, which is a continuation-in-part of U.S. patent application Ser. No. 08/873,413, which claims benefit of U.S. Provisional Patent Application Serial No. 60/019,931. filed Jun. 14, 1996, entitled "Fiber Reinforced Balloon."

FIELD OF THE INVENTION

This invention relates to the field of balloons that are useful in angioplasty and other medical uses.

BACKGROUND OF THE INVENTION

Catheters having inflatable balloon attachments have been used for reaching small areas of the body for medical treatments, such as in coronary angioplasty and the like. Balloons are exposed to large amounts of pressure. Additionally, the profile of balloons must be small in order to be introduced into blood vessels and other small areas of the body. Therefore, materials with high strength relative to film thickness are chosen. An example of these materials is PET (polyethylene terephthalate), which is useful for providing a non-compliant, high-pressure device. Unfortunately, PET and other materials with high strength-to-film thickness ratios tend to be scratch- and puncture- sensitive. Polymers that tend to be less sensitive, such as polyethylene, nylon, and urethane are compliant and, at the same film thickness as the non-compliant PET, do not provide the strength required to withstand the pressure used for transit in a blood vessel and expansion to open an occluded vessel. Non-compliance, or the ability not to expand beyond a predetermined size on pressure and to maintain substantially a profile, is a desired characteristic for balloons so as not to rupture or dissect the vessel as the balloon expands. Further difficulties often arise in guiding a balloon catheter into a desired location in a patient due to the friction between the apparatus and the vessel through which the apparatus passes. The result of this friction is failure of the balloon due to abrasion and puncture during handling and use and also from over-inflation.

SUMMARY OF THE INVENTION

The present invention is directed to a non-compliant medical balloon suitable for angioplasty and other medical procedures and which integrally includes very thin inelastic fibers having high tensile strength, and methods for manufacturing the balloon. The fiber reinforced balloons of the present invention meet the requirements of medical balloons by providing superior burst strength; superior abrasion-, cut- and puncture-resistence; and superior structural integrity.

More particularly, the invention is directed to a fiber-reinforced medical balloon having a long axis, wherein the balloon comprises an inner polymeric wall capable of sustaining pressure when inflated or expanded and a fiber/polymeric matrix outer wall surrounding and reinforcing the inner polymeric wall. The fiber/polymeric matrix outer wall is formed from at least two layers of fibers and a polymer layer. The fibers of the first fiber layer are substantially equal in length to the length of the long axis of the balloon and run along the length of the long axis. But "substantially equal in length" is meant that the fiber is at least 75% as long as the length of the long axis of the balloon, and preferably is at least 90% as long. The fiber of the second fiber layer runs radially around the circumference of the long axis of the balloon substantially over the entire length of the long axis. By "substantially over the entire length" is meant that the fiber runs along at least the center 75% of the length of the long axis of the balloon, and preferably runs along at least 90% of the length. The fiber of the second fiber layer is substantially perpendicular to the fibers of the first fiber layer. By "substantially perpendicular to" is meant that the fiber of the second fiber layer can be up to about 10 degrees from the perpendicular.

The invention is further directed to processes for manufacturing a non-compliant medical balloon. In one embodiment, a thin layer of a polymeric solution is applied onto a mandrel, the mandrel having the shape of a medical balloon and being removable from the finished product. High-strength inelastic fibers are applied to the thin layer of polymer with a first fiber layer having fibers running substantially along the length of he long axis of the balloon and a second fiber layer having fiber running radially around the circumference of the long axis substantially over the entire length of the long axis. The fibers are then coated with a thin layer of a polymeric solution to form a fiber/polymeric matrix. The polymers are cured and the mandrel is removed to give the fiber-reinforced medical balloon.

In another embodiment of the invention, a polymer balloon is inflated and is maintained in its inflated state, keeping the shape of the balloon. High-strength inelastic fibers are applied to the surface of the balloon, with a first fiber layer having fibers running substantially along the length of the long axis of the balloon and a second fiber layer having fiber running radially around the circumference of the long axis substantially over the entire length of the long axis. The fibers are then coated with a thin layer of a polymeric solution to form a fiber/polymeric matrix. The fiber/polymeric matrix is cured to give the fiber-reinforced medical balloon, which can then be deflated for convenience, until use.

In a presently preferred embodiment, a thin coating of an adhesive is applied to the inflated polymer balloon or to the polymer-coated mandrel prior to applying the inelastic fibers.

BRIEF DESCRIPTION OF THE DRAWINGS

FIG. 3 illustrates the positioning of the second layer of fiber over the first fiber layer. The fiber is wound radially around the long axis substantially over the entire length of the long axis of the balloon, each wrap being substantially equally spaced from the others. The fiber runs substantially perpendicular to the fibers of the first fiber layer.

FIG. 4 illustrates the positioning of the third layer of fiber over the second. fiber layer, in accordance with another embodiment.

DETAILED DESCRIPTION OF THE INVENTION

Figure 1:
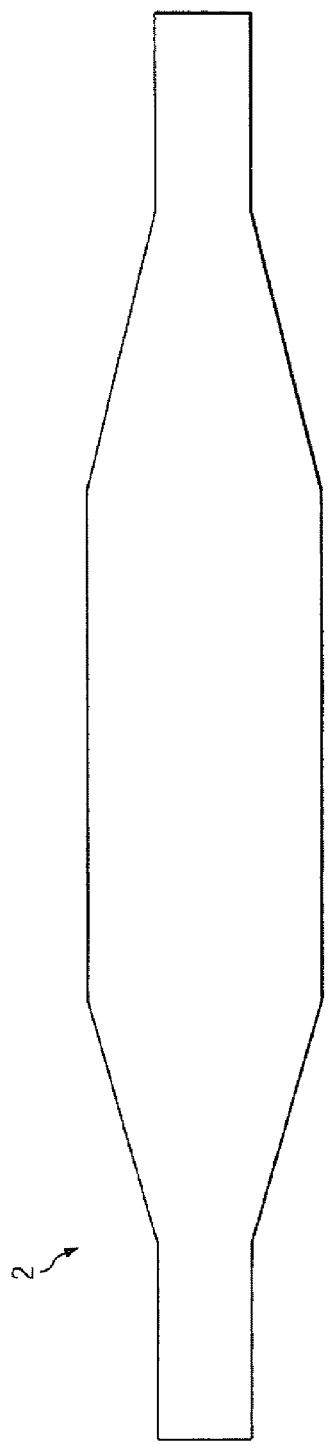
FIG. 1 illustrates an inflated standard medical balloon, which is used in this invention as the base of the final composite fiber-reinforced balloon.

Referring now to the drawings, wherein like reference numbers are used to designate like elements throughout the various views, several embodiments of the present invention are further described. The figures are not necessarily drawn to scale, and in some instances the drawings have been exaggerated or simplified for illustrative purposes only. One of ordinary skill in the art will appreciate the many possible applications and variations of the present invention based on the following examples of possible embodiments of the present invention.

Figure 2:
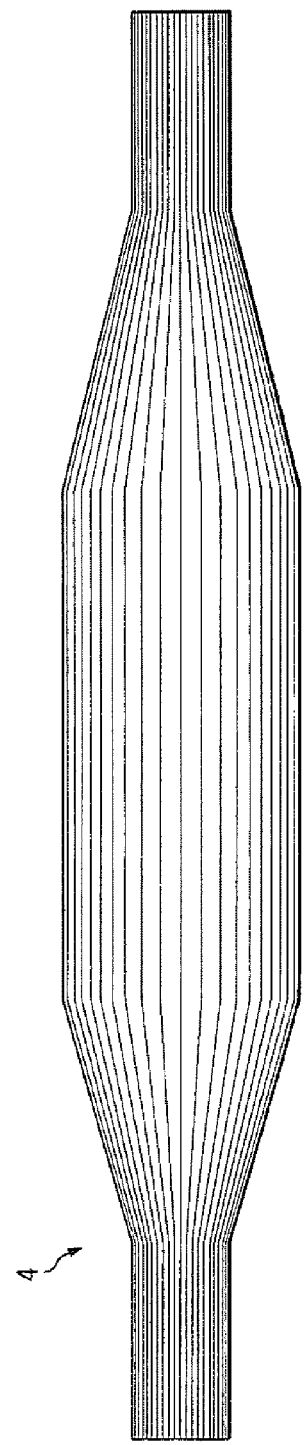
FIG. 2 illustrates an inflated standard medical balloon, which is used in this invention as the base of the final composite fiber-reinforced balloon.
Figure 5A:
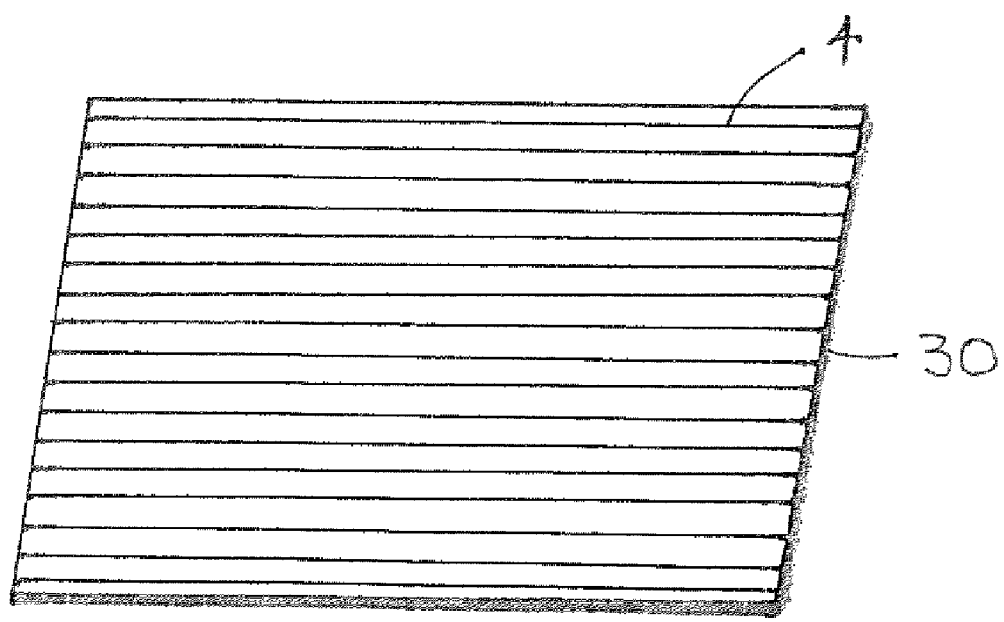
FIG. 5a illustrates a plurality of parallel fibers on a flat plate in accordance with one embodiment.
Figure 5B:
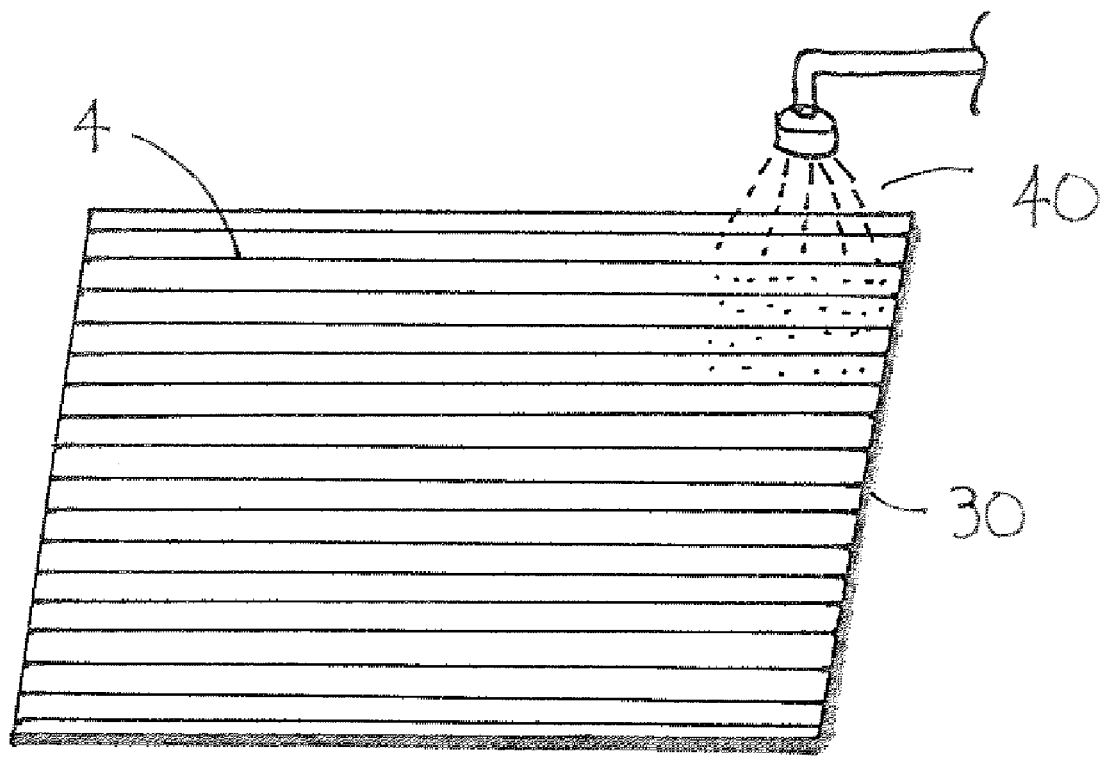
FIG. 5b illustrates coating the plurality of parallel fibers with a polymeric solution to create a fabric in accordance with one embodiment.
Figure 5C:
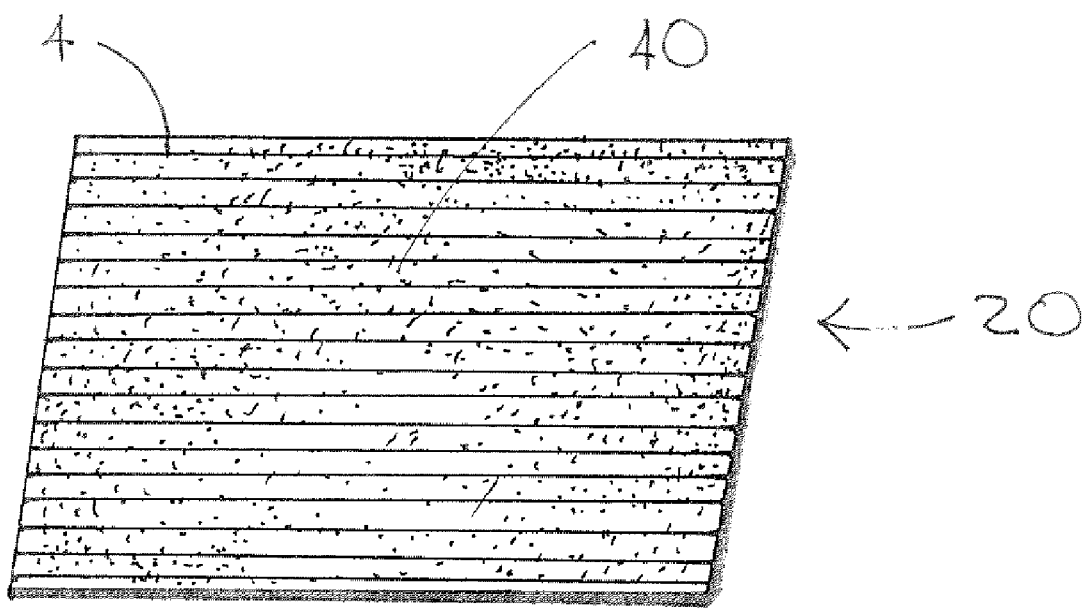
FIG. 5c illustrates the fabric having a polymeric solution coating in accordance with one embodiment.
Figure 5D:
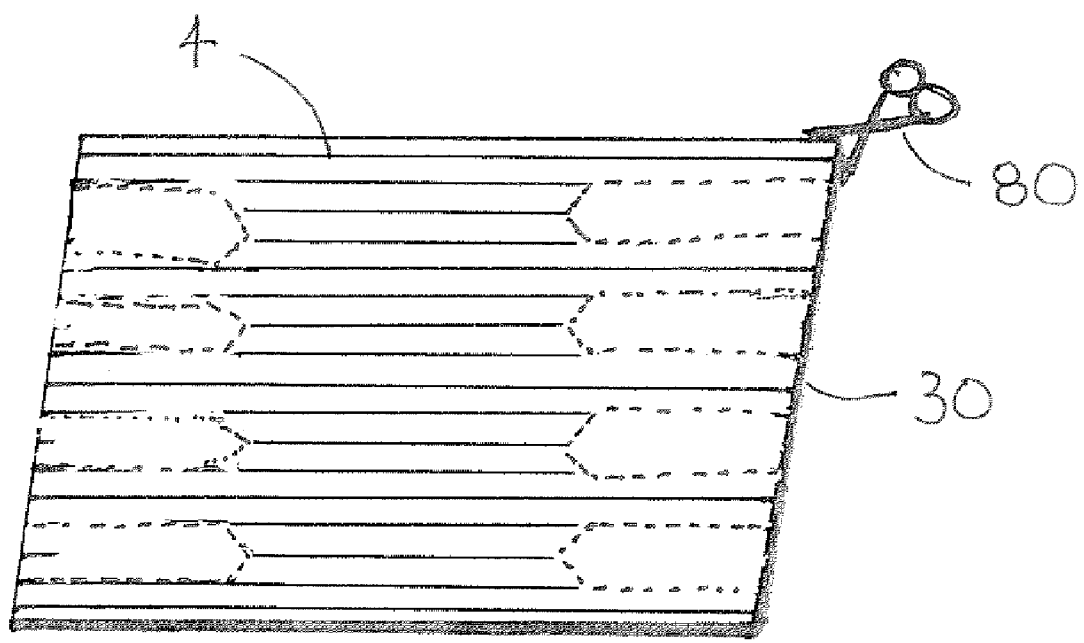
FIG. 5d illustrates cutting the fabric into a pattern in accordance with one embodiment.
Figure 5E:
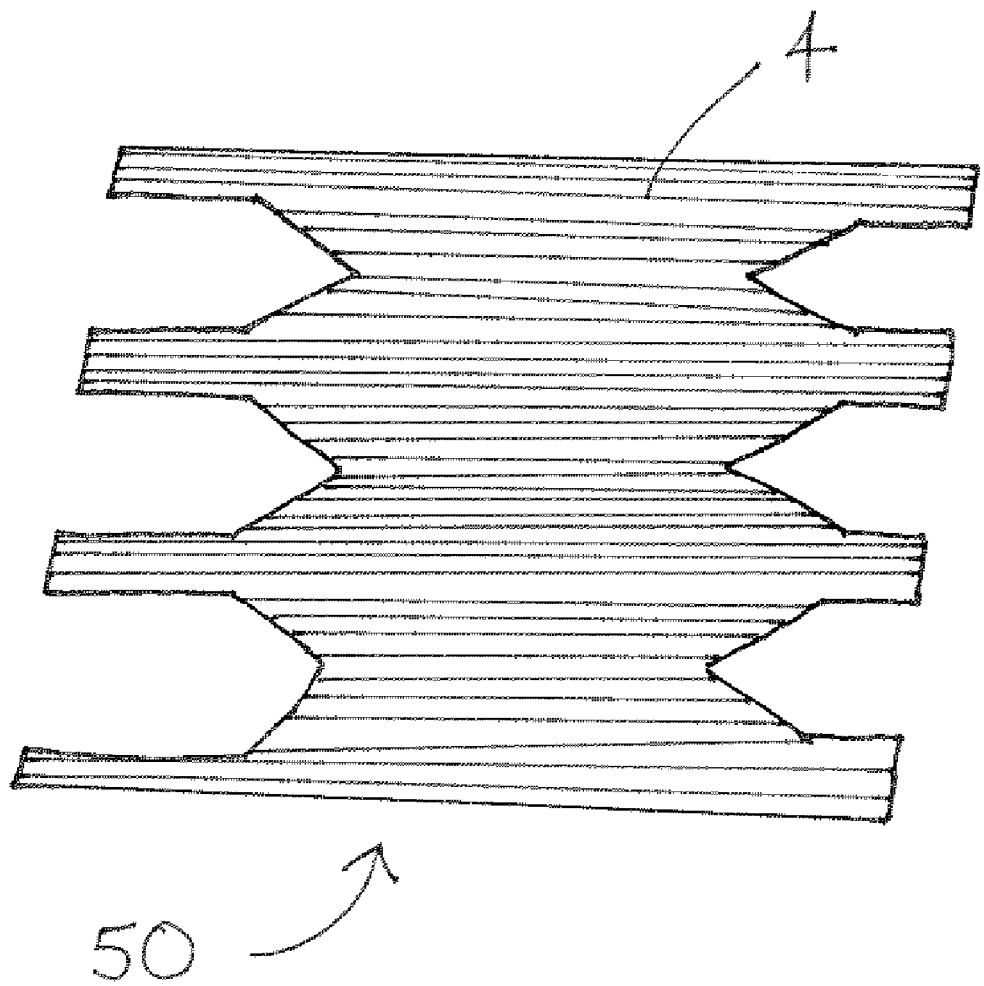
FIG. 5e illustrates a patterned fabric that may be wrapped around the base of the balloon or mandrel in accordance with one embodiment.
Figure 5F:
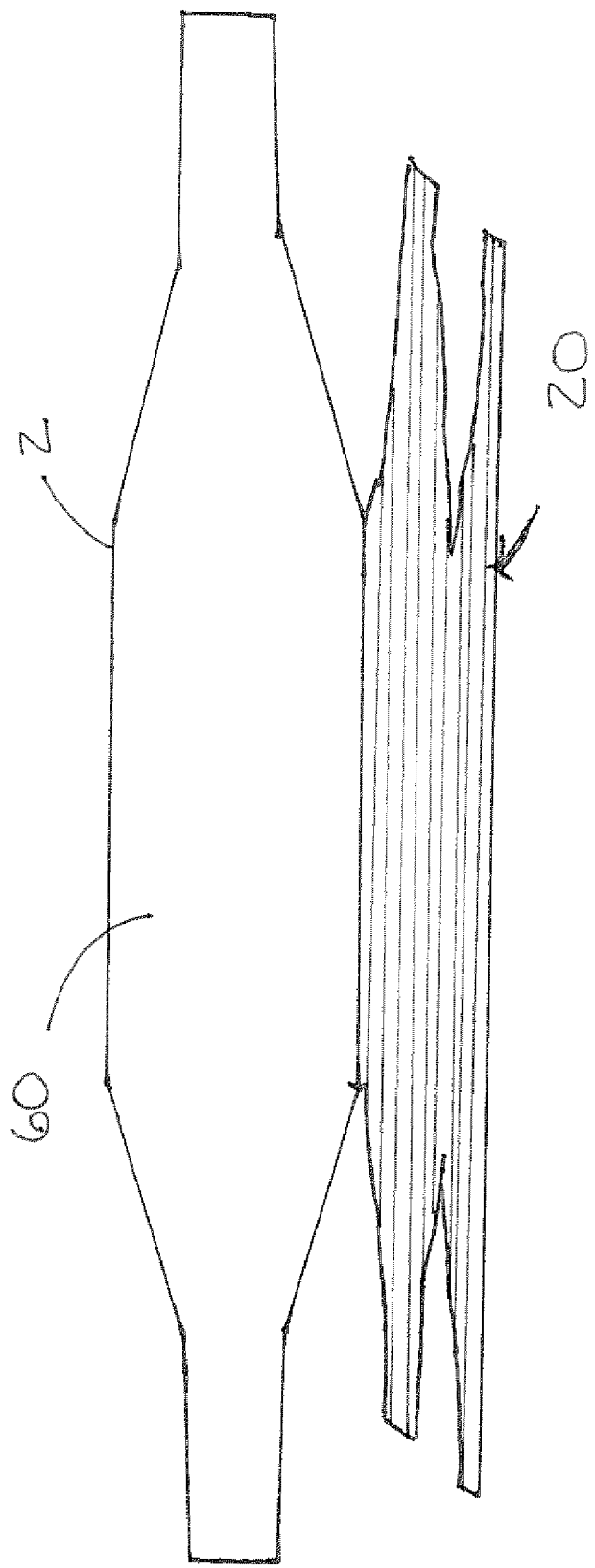
FIG. 5f illustrates the patterned fabric wrapped around the base of the balloon or mandrel in accordance with one embodiment.
Figure 5G:
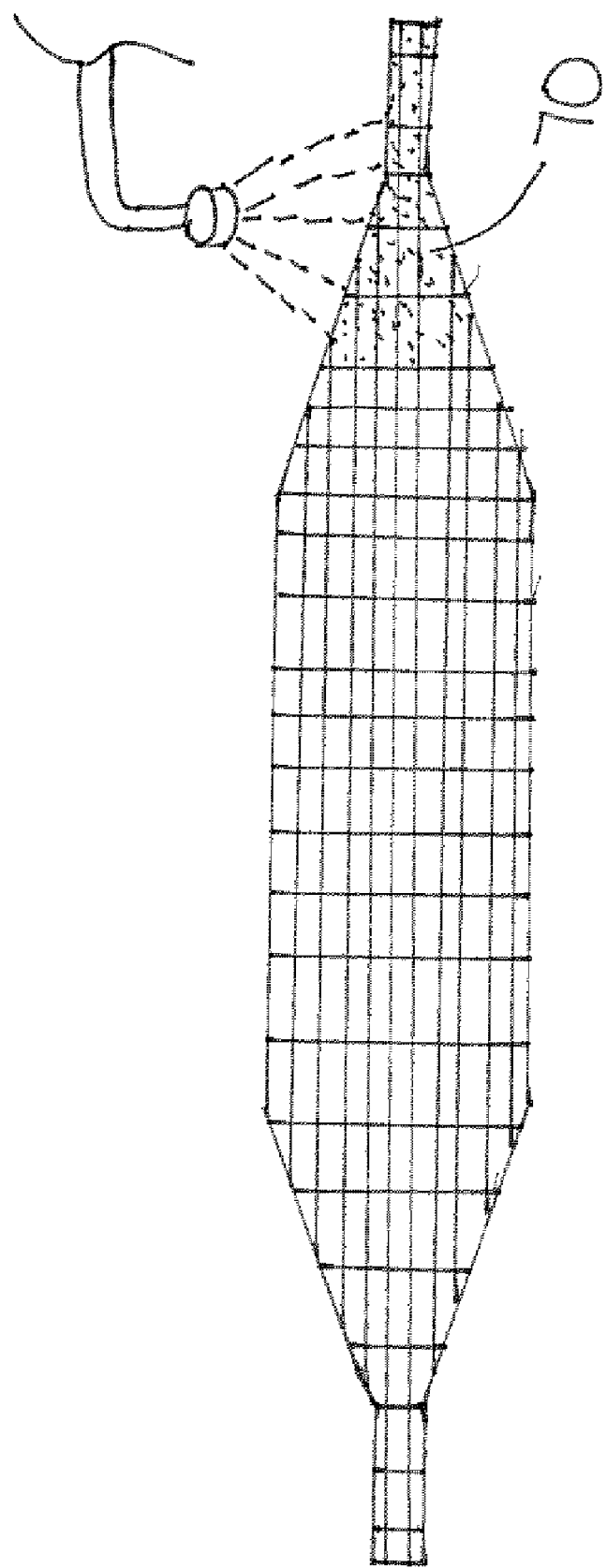
FIG. 5g illustrates a binding layer over a fabric layer and a second fiber in accordance with one embodiment.

A medical balloon in accordance with the present invention in one embodiment begins with an inflated polymeric balloon 2, as shown in FIG. 1, to which there is applied by hand or mechanically, inelastic fiber or filament 4, as shown in FIG. 2. This is sometimes referred to as the "primary wind." To assist in placement and retention of the fibers, there can be applied an adhesive to either the inflated balloon surface or to the fiber. The purpose of this first application of fiber is to prevent longitudinal extension (growth) of the completed balloon.

As shown in FIGS. 5a-5g, an alternate method of applying the longitudinal fibers involves first creating a fabric 20 of longitudinal fibers 4 by pulling taut multiple parallel fibers on a flat plate 30 and coating with a polymeric solution 40 to create a fabric. The fabric is then cut 80 into a pattern 50 such that it can be wrapped around the base balloon 60 or mandrel.

Next, a second application of inelastic fiber 6 is applied to the circumference of the balloon, as shown in FIG. 3. This is sometimes referred to as the "hoop wind." The purpose of the hoop wind is to prevent or minimize distension of the completed balloon diameter during high inflation pressures.

After the hoop wind is completed, the exterior of the fiber-wound inflated balloon is coated with a polymeric solution 40 and cured to form a composite, non-compliant fiber-reinforced medical balloon. The outer polymeric coating 70 of the fiber/polymeric matrix secures and bonds the fibers to the underlying inflated balloon so that movement of the fibers is restricted during deflation of the composite balloon and subsequent inflation and deflation during use of the balloon. The polymeric solution can be applied several times, if desired. The polymeric solution can use the same polymer as or a polymer different from the polymer of the inflated polymeric balloon 2. The polymers should be compatible so that separation of the composite balloon is prevented or minimized.

In a second method of making a medical balloon of the present invention, a removable mandrel having the shape that is identical to the shape of the inside of the desired balloon is used. A shape such as shown in FIG. 1 is suitable. The mandrel can be made of collapsible metal or polymeric bladder, foams, waxes, low-melting metal alloys, and the like. The mandrel is first coated with a layer of a polymer, which is then cured. This forms the inner polymeric wall of the balloon. Next, repeating the steps as described above, the primary wind and the hoop wind are placed over the inner polymer wall, followed by a coating with a polymeric solution and curing thereof to form a fiber/polymeric matrix outer wall. Finally, the mandrel is removed, by methods known in the art such as by mechanical action, by solvent, or by temperature change, to give the composite medical balloon of the invention.

In view of the high strength of the balloons of the present invention, it is possible to make balloons having a wall thickness less than conventional or prior art balloons without sacrifice of burst strength, abrasion resistence, or puncture resistance. The balloon wall thickness can be less than the thickness given in the examples hereinbelow.

In addition, the fiber-reinforced balloons of the present invention are non-compliant. That is, they are characterized by minimal axial stretch and minimal radial distention and by the ability not to expand beyond a predetermined size on pressure and to maintain substantially a profile.

Polymers and copolymers that can be used for the base balloon and/or the covering layer of the fiber/polymeric matrix include the conventional polymers and copolymers used in medical balloon construction, such as, but not limited to, polyethylene, polyethylene terephthalate (PET), polycaprolactam, polyesters, polyethers, polyamides, polyurethanes, polyimides, ABS copolymers, polyester/polyether block copolymers, ionomer resins, liquid crystal polymers, and rigid rod polymers.

The high-strength fibers are chosen to be inelastic. By "inelastic," as used herein and in the appended claims, is meant that the fibers have very minimal elasticity or stretch. Zero elasticity or stretch is probably unobtainable taking into account the sensitivity of modern precision test and measurement instruments, affordable costs and other factors. Therefore, the term "inelastic" should be understood to mean fibers that are generally classified as inelastic but which, nevertheless, may have a detectable, but minimal elasticity or stretch. High strength inelastic fibers useful in the present invention include but are not limited to, Kevlar, Vectran, Spectra, Dacron, Dyneema, Tenon (PBT), Zylon (PBO), Polyimide (PIM), ultra high molecular weight polyethylene, and the like. In a presently preferred embodiment, the fibers are ribbonlike; that is, they have a flattened to a rectangular shape. The fibers of the first fiber layer may be the same as or different from the fiber of the second fiber layer.

The most advantageous density of the fiber wind is determinable through routine experimentation by one of ordinary skill in the art given the examples and guidelines herein. With respect to the longitudinally-placed fibers (along the long axis of the balloon) of the first fiber layer, generally about 15 to 30 fibers having a fiber thickness of about 0.0005 to 0.001 inch and placed equidistant from one another will provide adequate strength for a standard-sized medical balloon. With respect to the fiber of the hoop wind, or second fiber layer, fiber having a thickness of about 0.0005 to 0.001 inch and a wind density within the range of about 50 to 80 wraps per inch is generally adequate. The fiber of the second fiber layer is preferably continuous and is, for a standard sized medical balloon about 75-100 inches long.

The longitudinally placed fibers should be generally parallel to or substantially parallel to the long axis of the balloon for maximum longitudinal stability (non-stretch) of the balloon. The fibers of the hoop wind should be perpendicular to or substantially perpendicular to the fibers placed longitudinally for maximum radial stability (non-stretch) of the balloon. This distributes the force on the balloon surface equally and creates "pixels" of equal shape and size. In the case where the fibers of the hoop wind are at a small acute angle (e.g.

about 10 degrees or more) to the longitudinal fibers, two hoop winds (in opposite directions) can be used for minimizing radial distension. FIG. 4 depicts a balloon having a second hoop wind 12.

EXAMPLES

The following examples are provided to illustrate the practice of the present invention, and are intended neither to define nor to limit the scope of the invention in any manner.

Example 1

An angioplasty balloon, as shown in FIG. 1, having a wall thickness of 0.0008 inch is inflated to about 100 psi, and the two open ends of the balloon are closed off. The inflation pressure maintains the shape (geometry) of the balloon in an inflated profile during the construction of the composite balloon. The balloon is a blow-molded balloon of highly oriented polyethylene terephthalate (PET). To the inflated balloon is applied a very thin coat of 3M-75 adhesive to hold the fibers sufficiently to prevent them from slipping out of position after placement on the balloon.

Kevlar® fibers are placed, by hand, along the length of the balloon as shown in FIG. 2 to provide the primary wind. Each of the fibers is substantially equal in length to the length of the long axis of the balloon. Twenty-four fibers are used, substantially equally spaced from each other. The fiber used for the primary wind has a thickness of 0.0006 inch.

Next, a hoop wind of Kevlar® fiber is applied radially around the circumference of and over substantially the entire length of the long axis of the balloon, as shown in FIG. 3. The fiber has a thickness of 0.0006 inch and is applied at a wind density of 60 wraps per inch.

The fiber-wound based PET balloon is then coated with a 10% solution of Texin® 5265 polyurethane in dimethylacetarnide (DMA) and allowed to cure at room temperature. Five additional coating of the polurethane solution are applied in about 6-hour increments, after which the pressure in the balloon is released. The resulting composite fiber-reinforced balloon is non-compliant and exhibits superior burst strength and abrasion and puncture resistance.

3M-75 is a tacky adhesive available from the 3M Company, Minneapolis, Minn. Kevlar® is a high strength, inelastic fiber available from the DuPont Company, Wilmington Del. Texin® 5265 is a polyurethane polymer available from Miles, Inc., Pittsburgh, Pa.

Example 2

The procedure of Example 1 was repeated with the exception that Vectran® fiber, having a thickness of 0.0005 inch is used in place of the Kevlar® fiber. The resulting composite balloon is axially and radially non-compliant at very high working pressures. The balloon has very high tensile strength and abrasion and puncture resistance.

Vectran® is a high strength fiber available from Hoechst-Celanese, Charlotte, N.C.

Example 3

A mandrel in the shape of a balloon as shown in FIG. 1 is made of a water-soluble wax. The wax mandrel is coated with a very thin layer (0.0002 inch) of Texin® 5265 polyurethane. After curing, adhesive and Vectran® fibers are applied, following the procedure of Example 1. Next, several coats of Texin® 5265 polyurethane as applied in Example 1. The wax is then exhausted by dissolving in hot water to give a non-compliant, very high strength, abrasion-resistant, composite fiber-reinforced balloon.

Example 4

The procedure of Example 3 is repeated using high strength Spectra® fiber in place of Vectran® fiber. Spectra® fiber is available from Allied Signal, Inc., Morristown, N.J.

Example 5

The procedure of Example 1 is repeated using Ultra High Molecular Weight Polyethylene (Spectra 2000)fiber, which has been flattened on a roll mill. To the flattened fiber is applied a thin coat of a solution of 1-MT Tecoflex® adhesive in a 60-40 solution of methylene chloride and methylethylketone. The fiber is applied to the balloon as in Example 1 using 30 longitudinal fibers, each substantially equal in length to the length of the long axis of the balloon, and a hoop wind of 54 wraps per inch. The fibers are then coated with the Tecoflex® solution.

Tecoflex® is supplied by Thermedics Inc., Woburn, Mass.

Example 6

A balloon-shaped solid mandrel made of a low melting temperature metal alloy is coated with a thin layer of Texin® 5265/DMA solution (10%). Vectran® fibers are applied as in Example 1, followed by coating with Texin®/DMA. The metal mandrel is melted out using hot water. A very high strength, abrasion-resistant, composite balloon is obtained, which is non-compliant.

Example 7

Following the procedures of Example 6, a mandrel is coated with a very thin layer of PIM polyimide (2,2-dimethylbenziciine) in solution in cyclopentanone. Polyimide fibers are applied, and the composite balloon is then completed with additional applications of the PIM solution. The mandrel is removed to give a high strength, puncture-resistant balloon having an extremely cohesive fiber/matrix composite wall that is resistant to delamination.

Example 8

A balloon is constructed as in Example 7, except that the longitudinal fibers are replaced by a longitudinally oriented thin film made of polyimide LARC-IA film (available from IMITEC, Schenectady, N.Y.). The film is cut into a mandrel-shaped pattern and applied to the mandrel, over which the polyimide hoop fibers and the PIM solution are applied.

Although the illustrative embodiment has been described in detail, it should be understood that various changes, substitutions and alterations can be made therein without departing from the spirit and scope of the invention as defined by the appended claims.

What is claimed is:

1. A non-compliant medical balloon comprising:
   a base layer;
   a fabric layer over said base layer, said fabric layer including a plurality of inelastic first fibers having a pattern of different lengths;
   wherein the plurality of inelastic first fibers are substantially parallel to a longitudinal axis of said non-compliant medical balloon.

2. The non-compliant medical balloon of claim 1, further comprising a second inelastic fiber over the fabric layer and substantially over an entire length of the longitudinal axis of the balloon.

3. The non-compliant medical balloon of claim 2, further comprising a plurality of second fibers parallel to said second fiber.

4. The non-compliant medical balloon of claim 3, wherein said second fiber has a thickness of about 0.0005 inch.

5. The non-compliant medical balloon of claim 3, wherein said second fiber has a wind density of approximately 50 wraps per inch.

6. The non-compliant medical balloon of claim 2, wherein the plurality of first fibers of the fabric layer and the second fiber form an angle.

7. The non-compliant medical balloon of claim 6, wherein said angle is substantially a right angle.

8. The non-compliant medical balloon of claim 6, wherein said angle does not change when the balloon changes from a deflated state to an inflated state.

9. The non-compliant medical balloon of claim 6, wherein said angle is about ten degrees.

10. The non-compliant medical balloon of claim 2, further comprising a binding layer substantially coating said fabric layer and said second fiber.

11. The non-compliant medical balloon of claim 10, wherein said binding layer is a polymeric coating.

12. The non-compliant medical balloon of claim 11, wherein said polymeric coating is formed of a copolymer.

13. The non-compliant medical balloon of claim 2, wherein said second fiber is substantially transverse to the longitudinal axis of the balloon.

14. The non-compliant medical balloon of claim 1, wherein said plurality of inelastic first fibers are divisible into a first and a second group, the first fibers of the first group extending substantially along an entire length of the balloon and the first fibers of the second group extending from a first conical portion of the balloon to a second conical portion of the balloon.

15. The non-compliant medical balloon of claim 14, wherein said plurality of inelastic first fibers each have a thickness of about 0.0005 inch.

16. The non-compliant medical balloon of claim 1, further comprising an adhesive layer adhering to said fabric layer.

17. A non-compliant medical balloon having a barrel portion disposed between two conical portions and two opposite cylindrical end portions extending from each of the two conical portions, comprising:
a fabric layer over said balloon, said fabric layer including a plurality of parallel first fibers having a pattern of different lengths;
a second fiber over said fabric layer;
a binding layer substantially coating said first fabric layer and said second fiber;
wherein said plurality of first fibers are substantially parallel to a longitudinal axis of said balloon and said second fiber is substantially perpendicular to the plurality of first fibers of the fabric layer.

18. The balloon of claim 17, wherein said plurality of first fibers are inelastic fibers.

19. The balloon of claim 17, wherein said plurality of first fibers are divisible into a first and a second group, the fibers of the first group extending substantially from a first cylindrical end portion to a second cylindrical end portion and the fibers of the second group extending a shorter distance from a first conical portion to a second conical portion.

20. The balloon of claim 17, further comprising an adhesive adhering to said fabric layer.

21. The balloon of claim 17, further comprising a plurality of second fibers parallel to said second fiber.

22. The balloon of claim 21 wherein said plurality of parallel second fibers are substantially transverse to the longitudinal axis of the balloon.

23. The balloon of claim 17, wherein the first fibers and the second fiber remain perpendicular when the balloon changes from a deflated state to an inflated state.

24. The balloon of claim 17, wherein said binding layer is a polymeric coating.

25. The balloon of claim 24, wherein said polymeric coating is formed of a copolymer.

26. The balloon of claim 17, wherein said fabric layer has a thickness of about 0.0005 inch.

27. The balloon of claim 17, wherein said second fiber has a thickness of about 0.0005 inch.

28. The balloon of claim 17, wherein said second fiber is wound around a circumference of the balloon with a wind density of approximately 50 wraps per inch.

29. The balloon of claim 17, wherein the first fibers and the second fiber are at an angle of about ten degrees from perpendicular.

30. The balloon of claim 17, further comprising a third fiber on said second fiber.

31. A non-compliant medical balloon having a barrel portion disposed between two conical portions and two opposite cylindrical end portions extending from each of the two conical portions, comprising:
a fabric layer comprising a pattern wrapped around the balloon, said pattern including a plurality of parallel first fibers;
a second fiber over said fabric layer;
a binding layer substantially coating said first fabric layer and said second fiber;
wherein said plurality of first fibers are substantially parallel to a longitudinal axis of said balloon and said second fiber meets the first fibers of the fabric layer at an angle.

32. The balloon of claim 31, wherein said angle is substantially a right angle.

33. The balloon of claim 31, wherein said angle is about 10 degrees from perpendicular.

34. The balloon of claim 31, wherein the angle does not change when the balloon changes from a deflated state to an inflated state.

35. A non-compliant medical balloon having a longitudinal axis, comprising:
an elongated body having generally conical end sections, said body comprising a base layer having an outer surface, and a fabric layer positioned over the outer surface of the base layer, said fabric layer including a plurality of inelastic fibers extending substantially parallel to the longitudinal axis.

36. The balloon of claim 35, wherein the body further includes at least one hoop fiber extending substantially perpendicular to the plurality of inelastic fibers.

37. The balloon of claim 35, wherein the base layer comprises a removable mandrel.

38. The balloon of claim 35, wherein the fabric layer comprises a cut-out pattern for wrapping around the base layer.

39. The balloon of claim 35, wherein the fabric layer comprises a coating for coating the inelastic fibers.

* * * * *